(12) United States Patent
Knolle et al.

(10) Patent No.: US 11,844,873 B2
(45) Date of Patent: Dec. 19, 2023

(54) SYSTEM AND METHOD FOR STERILITY TESTING OF RADIOACTIVE MATERIALS

(71) Applicant: CUP LABORATORIEN DR. FREITAG GMBH, Radeberg (DE)

(72) Inventors: Stefan Knolle, Radeberg (DE); Severine Protze, Radeberg (DE); Sven Jansen, Grosspostwitz (DE)

(73) Assignee: CUP LABORATORIEN DR. FREITAG GMBH, Radeberg (DE)

( * ) Notice: Subject to any disclaimer, the term of this patent is extended or adjusted under 35 U.S.C. 154(b) by 0 days.

(21) Appl. No.: 18/005,524

(22) PCT Filed: Jul. 28, 2021

(86) PCT No.: PCT/EP2021/071090
§ 371 (c)(1),
(2) Date: Jan. 13, 2023

(87) PCT Pub. No.: WO2022/023393
PCT Pub. Date: Feb. 3, 2022

(65) Prior Publication Data
US 2023/0256128 A1   Aug. 17, 2023

(30) Foreign Application Priority Data
Jul. 31, 2020   (EP) .................... 20188944

(51) Int. Cl.
*A61L 2/28*   (2006.01)
(52) U.S. Cl.
CPC ............ *A61L 2/28* (2013.01); *A61L 2202/21* (2013.01)

(58) Field of Classification Search
CPC .............................. A61L 2/28; A61L 2202/21
See application file for complete search history.

(56) References Cited

U.S. PATENT DOCUMENTS

| 4,416,995 A | * | 11/1983 | Amaral | C12Q 1/18 435/35 |
| 4,441,996 A | | 4/1984 | Hurst | |
| 4,604,351 A | * | 8/1986 | Amaral | C12Q 1/18 435/35 |

(Continued)

FOREIGN PATENT DOCUMENTS

| CN | 107935217 A | 4/2018 |
| DE | 3012085 A1 | 10/1981 |

(Continued)

OTHER PUBLICATIONS

International Search Report and Written Opinion of International Application No. PCT/EP2021/071090, dated Nov. 15, 2021, 19 pages.

*Primary Examiner* — Brian R Gordon
(74) *Attorney, Agent, or Firm* — Heslin Rothenberg Farley & Mesiti P.C.

(57) ABSTRACT

The invention relates to a system for testing the sterility of radioactive substances, to the use of the system for testing the sterility of radioactive substances, preferably radioactive pharmaceuticals and/or diagnostic agents, and to a method for testing the sterility of radioactive substances, wherein the system comprises an isolator (8) having a device for membrane filtration (9) and a filter bottle (1) surrounding the shield (5) against ionising radiation.

20 Claims, 1 Drawing Sheet

(56) References Cited

U.S. PATENT DOCUMENTS

| | | | |
|---|---|---|---|
| 2003/0180181 A1* | 9/2003 | Greib | A01N 1/0294 |
| | | | 422/20 |
| 2004/0009473 A1* | 1/2004 | Pease | C12Q 1/04 |
| | | | 435/8 |
| 2005/0098495 A1 | 5/2005 | Hughes | |
| 2007/0010702 A1* | 1/2007 | Wang | A61L 31/10 |
| | | | 424/422 |
| 2008/0060213 A1* | 3/2008 | Gehrmann | F26B 5/065 |
| | | | 206/530 |
| 2008/0191148 A1* | 8/2008 | Gibson | B65B 3/26 |
| | | | 250/432 PD |
| 2009/0212015 A1* | 8/2009 | Dougherty, Sr. | H05H 1/46 |
| | | | 118/723 R |
| 2016/0289249 A1* | 10/2016 | Kshirsagar | B01D 39/086 |
| 2017/0319728 A1* | 11/2017 | Schmitz | A61L 2/20 |
| 2019/0240622 A1* | 8/2019 | Pavlik | F04B 43/04 |
| 2020/0338497 A1* | 10/2020 | McDaniel | B01D 53/85 |
| 2022/0081518 A1* | 3/2022 | Tanaka | C08L 25/18 |
| 2022/0148746 A1* | 5/2022 | Charters | G01T 7/02 |
| 2023/0134732 A1* | 5/2023 | Prasetya | B67D 1/0431 |
| | | | 222/394 |

FOREIGN PATENT DOCUMENTS

| | | |
|---|---|---|
| EP | 2918684 A1 | 9/2015 |
| JP | 2013007634 A | 1/2013 |
| WO | 2012092394 A1 | 7/2012 |
| WO | 2017192191 A2 | 11/2017 |

* cited by examiner

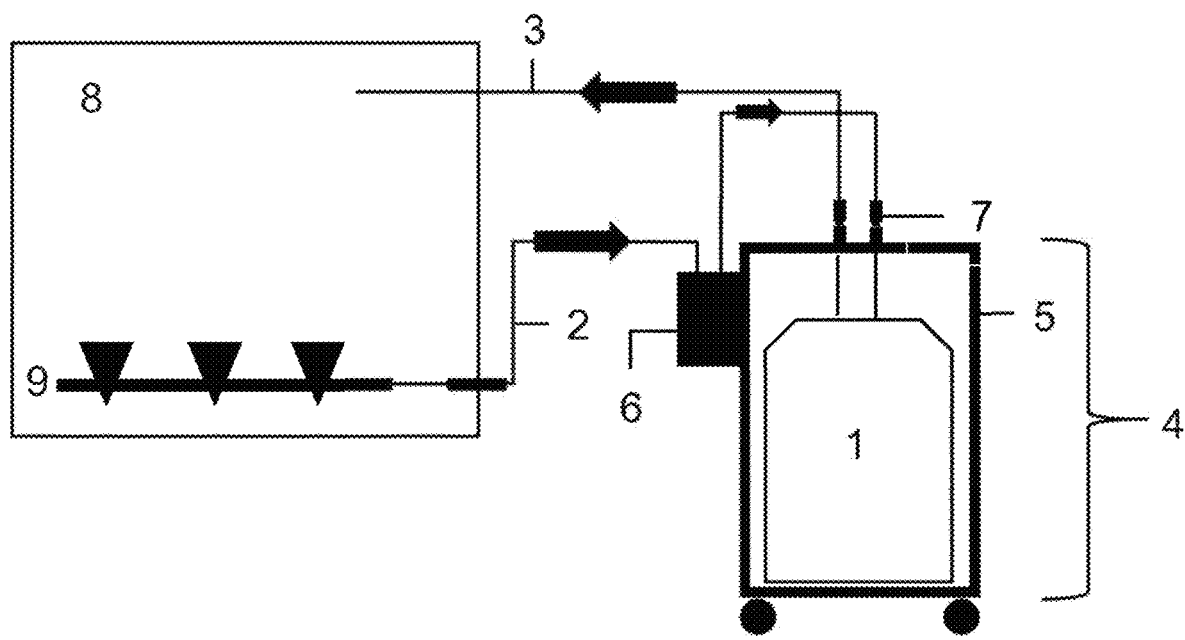

SYSTEM AND METHOD FOR STERILITY TESTING OF RADIOACTIVE MATERIALS

CROSS REFERENCE TO RELATED APPLICATIONS

This application is a national stage filing under section 371 of International Application No. PCT/EP2021/071090, filed on Jul. 28, 2021, and published on Feb. 3, 2022 as WO 2022/023393, which claims priority to European Application No. 20188944.1, filed on Jul. 31, 2020. The entire contents of WO 2022/023393 are hereby incorporated by reference herein.

The invention relates to a system for testing the sterility of radioactive substances, to the use of the system for testing the sterility of radioactive substances, preferably radioactive pharmaceuticals and/or diagnostic agents, and to a method for testing the sterility of radioactive substances.

PRIOR ART

Part of the quality control of drugs and medical products produced under aseptic conditions for use on humans or animals provides for sterility testing according to the European Pharmacopoeia (Ph. Eur. 2.6.1—Sterility testing) or U.S. Pharmacopeia (USP)<71>).

Drugs and medical products include aqueous solutions, soluble powders, oils and oily solutions, ointments and creams, infusion bags, implants, for example heart valves or stents; and surgical suture material.

What is decisive for testing the sterility of drugs and medical devices is compliance with aseptic testing conditions, which is often ensured by the use of an isolator (sterile box) for contamination prevention.

Sterility testing is preferably carried out by the membrane filtration method. The membrane filtration method is a method for the mechanical enrichment of microorganisms from any quantity of a filterable test material. Even with minimal germ content, this method enables exact germ count determinations. A certain volume of a liquid is filtered through a membrane filter with a defined pore size, wherein the germs contained therein are retained on the filter surface. The filter is subsequently brought to a nutrient medium. The nutrients of the nutrient medium enable the growing of the individual germs into diagnosable colonies.

Document EP 2 918 684 A1 discloses a rapid sterility microassay for determining living microorganisms in a pharmaceutical composition comprising the provision of a filterable pharmaceutical composition, providing the filtration of the pharmaceutical composition by at least three membranes on which the pharmaceutical composition is deposited and cultivation of the three membranes on a solid culture medium under aerobic and anaerobic conditions.

Alternatively, the contaminated filters can be transferred into liquid nutrient media. Multiplication of microorganisms is indicated, depending on the medium, either by turbidity or, if indicator dyes are contained in the medium, by color changes.

The development of membrane filtration for separating microorganisms or cells from solutions relates in particular to the production of novel filter materials.

U.S. Pat. No. 4,441,996 A discloses a system for producing drinking water from bacterially contaminated cold water by means of a porous submicron filter under a pressurized supply comprising the porous submicron filter, a receiving chamber and an opening for the sterile outlet of the filtered water.

US 2005/0098495 A1 discloses a separation material and a method for cleaning fluids, including water or gases, chemical and microbiological contaminants. The separation material comprises a particulate filter material and a first and a second binder, whereby a porous filter material with a non-porous coating is obtained.

In the case of non-filterable solutions, the medicament or medical product is dissolved or diluted in aqueous or oily solvents and then filtered. In this case, the solvent used must not negatively influence the test for sterility, and in particular have no antimicrobial properties.

In the case of non-soluble products (e.g., implants, surgical suture material), the test is carried out in the direct loading process, wherein the product is introduced directly into the nutrient medium.

One problem has hitherto been the sterility testing of radioactive drugs.

The performance of the membrane filtration method is problematic due to the handling and storage of the radioactive filtrate.

For this reason, the testing for sterility of radioactive substances, in particular of radioactive pharmaceuticals and/or diagnostic agents, frequently takes place by means of the direct loading process. Disadvantageous here is that the test is limited to a small amount of the sample, since the radioactivity is problematic for the germ testing. Furthermore, the sterility testing of radioactive pharmaceuticals does not meet the legal requirements according to the European Pharmacopoeia (Ph. Eur. 2.6.1—Sterility testing) or U.S. Pharmacopeia (USP <71>).

Alternatively, the sterility of radioactive substances is tested by the membrane filter method after the radioactivity has subsided, in particular after approximately three months.

However, this method can only be carried out in the case of radioactive substances with short-lived nuclides. Long-lasting nuclides are excluded due to the large expenditure of time. Further disadvantageous is that sterility testing is of little significance several months after the production of the radioactive substances, in particular due to the negative influence of the radioactivity on germ growth.

Known methods for the filtration of radioactive solutions have exclusively the task of removing the radioactive compounds or selectively removing certain radioactive compounds.

CN 10 7935 217 A discloses a system for separating radon from water, comprising an automatic feed unit, an underground sample tank, a stirred mixing vessel, a ceramic filter unit and a wastewater tank. The sample or the water to be purified is conveyed by means of a pump. Furthermore, the system comprises an overpressure line.

JP 2013 007 634 A discloses a water purification device for removing radioactive substances from tap water by means of a layer of zeolite and/or neolite for removing cesium, and a weathered granular granite layer for removing chlorine. The device further comprises an inlet, a sample tank, a pump and a pressure indicator.

A disadvantage of these devices is that the radioactive substances cannot be separated off by any microorganisms present.

Document WO 2017/192191 A2 discloses a system for transferring radionuclide generator columns from a production line to a clean room environment comprising a radiation containment chamber, an isolator connected to the radiation containment chamber, a rotating transfer door arranged between the radiation containment chamber and the isolator, and a hollow space for receiving a radionuclide generator column assembly, and an antimicrobial steam generator connected to the isolator, wherein the transfer door is configured to rotate while antimicrobial steam is being introduced into the isolator by the antimicrobial steam generator.

WO 2017/192191 A2 describes membrane filtration or direct inoculation for the sterility testing of elution columns using a sterile plastic canister comprising a sterilisation filter for membrane filtration (paragraphs [0044] and [0045]). In particular, a column unit is eluted during the sterility testing and the eluted product liquid is led through the plastic canister which contains a sterilisation filter at the canister outlet. The canister is then filled with a suitable growth medium and incubated to promote the growth of the microorganisms present.

Document DE 30 12 085 A1 discloses a device for testing the sterility of fluids having at least one closed bushing comprising an inlet for the fluid to be investigated, for a flushing solution and a nutrient medium, an outlet and a membrane filter.

Document WO 2012/092394 A1 discloses a closed system for the aseptic delivery of finished radiopharmaceuticals into receiving vessels such as a quality control vial, a sterility vial and/or end product vial, comprising a bulk product vial, a peristaltic pump connected to the bulk product vial and operated by a stepper motor, a metering manifold assembly coupled to the peristaltic pump and coupled to the at least one end product vial, an optional quality testing station, and an optional waste collection system. The peristaltic pump is configured such that a predefined amount of the bulk product can be transferred from the bulk product vial into the final product vial.

WO 2012/092394 A1 discloses a shield of the radiopharmaceutical products, in particular a shield around the bulk product vial.

The object of the present invention is thus to provide a system and a method for the sterility testing of radioactive substances.

The object is solved by the features of the independent claims. Advantageous embodiments are specified in the dependent claims.

According to the invention, the object is solved by a system for testing the sterility of radioactive substances, comprising
 i. a filtrate bottle comprising at least one liquid-conveying line and at least one pressure equalizing line, and
 ii. at least one trolley, wherein the trolley is suitable for receiving the filtrate bottle, wherein the trolley is movable, wherein at least the filtrate bottle is surrounded by a shield against ionising radiation,
 iii. a vacuum pump, wherein the vacuum pump is suitable for pumping filtrate containing the radioactive substance into the filtrate bottle,
 iv. at least one self-sealing connecting piece which can be connected to the isolator and/or a pumping device, and
 v. wherein the isolator is connected to the trolley via the at least one liquid-conveying line and the at least one pressure equalizing line.

Advantageously, the system according to the invention can be connected to an isolator and/or a decay pool. The system according to the invention advantageously enables the membrane filtration of a radioactive substance while protecting the environment from damaging effects of the radioactive materials to be processed, in particular personal protection, and thus the testing of the sterility of the radioactive materials.

By the term "radioactive substance" is meant a pure substance or a composition or a mixture of different substances comprising at least one radioactive element, such as $^{123}$I or $^{177}$Lu.

By the term "filtrate bottle" is meant a bottle, for example a wide-neck chemical bottle, which has at least one at least liquid-tight feedthrough for a liquid-conveying line and at least one further at least liquid-tight feedthrough for a pressure equalizing line. Advantageously, the filtrate bottle can be connected via the liquid-conveying line to a device for membrane filtration.

In embodiments, the filtrate bottle is made of glass, in particular borosilicate glass; plastic and/or metal. The filtrate bottle is expediently dimensionally stable with regard to overpressure and negative pressure.

In embodiments, the filtrate bottle has a capacity in the range of 200 ml to 10 l, preferably a capacity in the range of 1 l to 5 l, particularly preferably a capacity of 3 l.

By the term "pressure equalizing line" is meant a line for compensating the gas pressure between the filtrate bottle and an isolator or a ventilation system, in particular a laminar air flow system.

In further embodiments, the liquid-conveying line and the at least one pressure equalizing line are a line which is stable in relation to overpressure and negative pressure, preferably made of rubber and/or metal, particularly preferably of stainless steel.

In embodiments, the filtrate bottle has a screw-on cap which has at least one feedthrough for the liquid-conveying line and at least one feedthrough for the pressure equalizing line.

By the term "trolley" is meant a movable cart which is able to spatially move at least the filtrate bottle, preferably from an isolator to a decay pool and/or from a decay pool to an isolator.

In embodiments, the trolley has castors or wheels on the underside, preferably at least two castors, particularly preferably four castors.

By the term "shield against ionising radiation" is meant a housing which is capable of reducing the radiation intensity of ionising radiation of a radioactive substance, in particular of alpha, beta and gamma radiation, outside the housing by at least 90%, preferably by 100%.

In embodiments, the shield against ionising radiation is attached to at least one longitudinal side of the filtrate bottle. The shield against ionising radiation preferably completely surrounds the filtrate bottle.

In embodiments, the shield against ionising radiation has a metal with a thickness of at least 40 mm, preferably with a thickness in the range of 40 mm to 100 mm, particularly preferably with a thickness in the range of 40 mm to 50 mm. The thickness is expediently dependent on the selection of the metal.

In embodiments, the metal in the shield against ionising radiation is selected from lead, stainless steel, steel, copper, tungsten or uranium, particularly preferably from lead, stainless steel and steel.

In further embodiments, the shield against ionising radiation further comprises a plexiglass layer.

It is advantageous for personal protection to be ensured by the shield against ionising radiation.

According to the invention, the system according to the invention further comprises a vacuum pump, wherein the vacuum pump is suitable for pumping filtrate containing the radioactive substances into the filtrate bottle. The vacuum pump is preferably connected to the liquid-conveying line. Advantageously, the vacuum pump creates a negative pressure at least in the liquid-conveying line, whereby no escape of the filtrate containing the radioactive substances is possible.

In embodiments, the filtrate bottle has a liquid fill-level meter, wherein the liquid fill-level meter delivers a visual and/or acoustic signal at a predefined fill level of the filtrate. In embodiments, liquid fill-level meters give a visual and/or acoustic signal at a fill level of the filtrate in the range of 60% (v/v) to 90% (v/v) with respect to the maximum filling volume, preferably at a fill level of the filtrate of 80% (v/v) with respect to the maximum filling volume.

The liquid fill-level meter advantageously provides a visual and/or acoustic signal at a predefined fill level of the filtrate, until an interruption of the current supply to the vacuum pump.

According to the invention, the system according to the invention further comprises at least one self-sealing connecting piece which can be connected to an isolator and/or a pumping device. The at least one self-sealing connecting piece expediently connects the filtrate bottle, in particular the liquid-conveying line and/or the pressure equalizing line, to the isolator and/or to the pumping device, in particular a decay pool.

In embodiments, the self-sealing connecting piece has a pipe screw fitting, for example a clamping screw fitting or a clamping ring screw fitting or a cutting ring screw fitting or flanged screw fitting. Advantageously, the self-sealing connecting pieces enable a drip-free separation of the filtrate bottle from an isolator and/or the decay pool.

The system according to the invention further comprises an isolator, wherein the isolator is connected to the trolley via the at least one liquid-conveying line and the at least one pressure equalizing line.

Advantageously, the isolator protects the environment from damaging effects of the radioactive materials to be processed, in particular a personal protection is enabled.

In preferred embodiments, the isolator is a sterile box. By the term "sterile box" or also "glove box" is meant a system which is hermetically sealed and gas-tight with respect to the surrounding working chamber. A defined atmosphere for processing radioactive substances can be produced within the sterile box.

In embodiments, a Lexan or glass sheet is present on at least one side of the isolator, wherein the interior space is visible through the Lexan or glass sheet.

In embodiments, the isolator further comprises stainless steel.

In embodiments, the isolator has at least two feedthroughs, which permit reaching into the system by means of rubber or plastic gloves.

In embodiments, the isolator has at least one evacuatable chamber or lock.

In embodiments, the isolator further comprises a gas inlet, wherein the gas inlet is designed for the supply of inert gas and/or hydrogen peroxide for sterilising the isolator.

In embodiments, the connection between the isolator and/or the pumping device is designed with the trolley as a beam trap.

Expediently, the feedthrough of the liquid-conveying line and/or the pressure equalizing line is implemented as a beam trap by the shield against ionising radiation.

According to the invention, the isolator comprises a device for membrane filtration.

In embodiments, the device for membrane filtration comprises at least one membrane filter made of cellulose acetate or cellulose nitrate and/or having pores in the range from 0.2 µm to 0.45 µm.

In embodiments, the device for membrane filtration has a capacity in the range from 50 ml to 250 ml, preferably a capacity of 100 ml.

A further aspect of the invention relates to the use of a system according to the invention for the sterility testing of radioactive substances, preferably radioactive pharmaceuticals and/or diagnostic agents, such as Luthatera® or Loflupan®. Testing the sterility of radioactive substances by means of the system according to the invention is preferably carried out according to the European Pharmacopoeia (Ph. Eur. 2.6.1—Sterility testing) or U.S. Pharmacopeia (USP <71>).

In embodiments, a system is used, comprising
i. a filtrate bottle comprising at least one liquid-conveying line and at least one pressure equalizing line, and
ii. at least one trolley, wherein the trolley is adapted to receive the filtrate bottle,
wherein the trolley is movable,
wherein at least the filtrate bottle is surrounded by a shield against ionising radiation,
iii. a vacuum pump, wherein the vacuum pump is suitable for pumping filtrate containing the radioactive substance into the filtrate bottle,
iv. at least one self-sealing connecting piece which can be connected to the isolator and/or a pumping device, and
v. wherein the isolator is connected to the trolley via the at least one liquid-conveying line and the at least one pressure equalizing line
for testing the sterility of radioactive substances, preferably radioactive pharmaceuticals and/or diagnostic agents.

A further aspect of the invention relates to a method for testing the sterility of radioactive substances, comprising the steps of
a) membrane filtration of a solution of a radioactive substance by means of a device for membrane filtration comprising at least one membrane filter in an isolator, and suction through a system comprising
a filtrate bottle comprising at least one liquid-conveying line and at least one pressure equalizing line, and
at least one trolley, wherein the trolley is suitable for receiving the filtrate bottle, wherein the trolley is movable,
wherein at least the filtrate bottle is surrounded by a shield against ionising radiation,
a vacuum pump, wherein the vacuum pump is suitable for pumping into the filtrate bottle filtrate containing the radioactive substance,
at least one self-sealing connecting piece which can be connected to the isolator and/or to a pumping device,
wherein the isolator is connected to the trolley via the at least one liquid-conveying line and the at least one pressure equalizing line
b) cultivation of the membrane filters in a culture medium, and
c) testing the culture medium on microorganisms.

In embodiments, the method takes place in the sequence of steps a), b) and c).

Advantageously, microorganisms are selectively separated from the solution of a radioactive substance by membrane filtration and the radioactive material is preferably filtered off with the filtrate by suction. Furthermore, the method according to the invention or the use of the system according to the invention ensures simple and safe handling of the radioactive materials.

The method according to the invention is expediently carried out using sterile materials, in particular a sterile membrane filter and sterile culture medium, and a sterilised isolator.

In embodiments, the solution of a radioactive substance is an aqueous solution, alcoholic solution and/or oil-based solution.

In embodiments, the solution of a radioactive substance is obtained by dissolving at least one solid or pasty radioactive substance with a solvent, in particular with an aqueous, alcoholic and/or carboxylic acid ester-based solvent.

In embodiments, the solution of a radioactive substance is obtained by diluting an oil-based solution of a radioactive substance with a solvent, in particular with an aqueous, alcoholic and/or carboxylic acid ester-based solvent.

Expediently, the solvent has no antimicrobial property.

Preferably, a solid or pasty radioactive substance is dissolved or an oil-based solution is diluted with isopropyl myristate.

In embodiments, membrane filtration in step a) is carried out with at least one membrane filter made of cellulose acetate or cellulose nitrate and/or having pores in the range from 0.2 μm to 0.45 μm.

In embodiments, membrane filtration in step a) is performed with an aqueous solution, a weakly alcoholic solution or an oil-based solution with at least one cellulose nitrate filter.

In embodiments, membrane filtration in step a) is carried out in a strongly alcoholic solution with at least one filter of cellulose acetate.

In embodiments, membrane filtration in step a) takes place under slight negative pressure. By slight negative pressure is meant a pressure in the range from 5 kPa to 30 kPa. The escape of substances from the isolator is advantageously prevented by the slight negative pressure.

In embodiments, the process according to the invention further comprises at least one rinsing step after step a), wherein the membrane filter is rinsed at least once with a solvent, in particular an aqueous, alcoholic and/or carboxylic acid ester-based solvent. In preferred embodiments, the method according to the invention after step a) further comprises one to five rinsing steps, more preferably three rinsing steps.

In embodiments, the cultivation of the membrane filters takes place in step b) in a culture medium in an incubator.

By the term "culture medium" is meant a liquid or solid medium which serves to grow or culture microorganisms.

In embodiments, the cultivation of the membrane filters takes place in step b) on a solid culture medium (nutrient soil) or in a liquid culture medium (nutrient medium).

In preferred embodiments, the cultivation of the membrane filters in step b) takes place on agar plates.

By the term "incubator" is meant an adjustable temperature control device which is capable of maintaining constant humidity and temperature conditions in the interior.

In embodiments, the cultivation of the membrane filters in step b) takes place at a temperature in the range from 20° C. to 37° C., preferably at a temperature in the range from 20° C. to 25° C. or in the range from 30° C. to 35° C.

In embodiments, the cultivation of the membrane filters in step b) takes place at an air humidity in the range from 30% to 70%.

In embodiments, the cultivation of the membrane filters in step b) takes place under aerobic and/or anaerobic conditions.

In embodiments, the cultivation of the membrane filters in step b) takes place for a duration of at least 14 days, preferably for 14 days.

In embodiments, the testing of the culture medium for microorganisms in step c) takes place by visual determination of a colony formation on a solid culture medium.

In alternative embodiments, the culture medium is tested on microorganisms in step c) by visual determination of a turbidity in a liquid culture medium.

In embodiments, the culture medium is tested on microorganisms in step c) at least once, preferably after cultivation of the membrane filters for a duration of 14 days.

In further embodiments, the testing of the culture medium for microorganisms in step c) takes place at least twice, preferably after cultivation the membrane filters for a duration of 7 days and 14 days.

In embodiments, the method according to the invention further comprises extracting the solution of a radioactive substance from the filtrate bottle by suction and allowing the solution of a radioactive substance to decay in a decay pool.

In embodiments, the method according to the invention further comprises the sterilisation of the isolator before step a) and/or after step c). In embodiments, the isolator is sterilised by gassing with hydrogen peroxide. Advantageously, by gassing with hydrogen peroxide, a full-area decontamination of all materials introduced into the working area or into the lock is effected.

Expediently, the sterilisation of the isolator by gassing with hydrogen peroxide comprises the subsequent restoration of a hydrogen peroxide-free atmosphere, so that a test for sterility can take place with the exclusion of false negative results.

In embodiments, the method according to the invention further comprises the comparison with suitable controls, in particular at least one positive control, at least one negative control and/or at least one environment control.

By the term "positive control" is meant a sample comprising microorganisms capable of reproduction, which shows a "positive result" according to the method according to the invention, i.e. a growth of microorganisms. Positive controls advantageously enable the exclusion of false negative results.

In embodiments, the positive control comprises culture medium and microorganisms capable of reproduction.

By term "negative control" is meant a sample which, according to the method according to the invention, in particular steps a), b) and c), shows a "negative result", i.e. no growth of microorganisms. Advantageously, negative controls enable the exclusion of false positive results.

In embodiments, the negative control is culture medium without any addition of microorganisms.

By term "environment control" is meant a sample which shows the quality of the air and the surfaces of the system according to the invention.

The comparison is expediently carried out using suitable controls, preferably the at least one negative control and/or the at least one environment control, in the case of a first performance of the method according to the invention and/or in the case of a change in the cultivation conditions.

The comparison is expediently carried out using suitable controls, preferably with the at least one positive control, with each sample, i.e. the solution of a radioactive substance.

For the realisation of the invention, it is also expedient to combine the above-described embodiments and features of the claims, in particular to apply the features of the system according to the invention to the use according to the invention and the method according to the invention.

EXEMPLARY EMBODIMENTS

The invention is explained in more detail below with reference to a number of exemplary embodiments and associated FIGURES. The exemplary embodiments are intended to describe the invention without limiting it.

FIG. 1 shows a schematic illustration of the system according to the invention for testing the sterility of radioactive substances comprising a filtrate bottle 1, a liquid-conveying line 2 and a pressure equalizing line 3, a movable trolley 4, wherein the filtrate bottle 1 is located within the movable trolley 4 and wherein the movable trolley 4 has four castors on the underside. The housing of the trolley 4 represents a shield against ionising radiation 5. The trolley further comprises a vacuum pump 6. The fluid-conveying line 2 and the pressure equalizing line 3 feature a self-sealing connecting piece 7 and are connected to the isolator 8, in particular the liquid-conveying line 2 is connected to a device for membrane filtration 9 within the isolator 8.

EXEMPLARY EMBODIMENT

Sterile Testing of a 177Lu-DOTA-TOC Solution by Means of a System According
To the Invention A $^{177}$Lu-DOTA-TOC solution with an activity of about 7000 MBq and the following composition:
- 13 mg sodium ascorbate
- 31 mg sodium acetate
- 4 mg 2,5-dihydroxybenzoic acid
- 6 ml 0.04 M acetic acid
- 10 ml 0.9% sodium chloride solution
- 115 µg $^{177}$Lu-DOTA-TOC in 115 µl 0.04 M acetic acid is introduced into the isolator, in particular the sterile box, and filtered completely or partially via membrane filters (cellulose nitrate, pore size 0.45 µm). The membrane filter is then rinsed with 50 ml to 300 ml of buffer. The membrane filter is then in each case added to 100 ml of casein soya peptone broth and 100 ml of thioglycolate broth. The membrane filters are incubated in the culture medium for 14 days, in casein soya peptone broth at a temperature in the range from 20° C. to 25° C. and in thioglycolate broth at a temperature in the range from 30° C. to 35° C.

The evaluation is effected by visual assessment of the turbidity. In the case of an absence of turbidity, the sample is negative for microorganism growth and is thus sterile. In the case of turbidity, the sample is positive for microorganism growth and is thus non-sterile.

The sample solution in the filtrate bottle comprising 177Lu-DOTA-TOC, which is pumped off by means of the system according to the invention, is transported with the trolley to a decay pool and pumped out after the connection of the liquid-conveying line to the decay pool. The solution is left for at least 60 days in the decay pool until decay below the free limit.

REFERENCE SIGNS

1 Filtrate bottle
2 Liquid-conveying line
3 Pressure equalizing line
4 Trolley
5 Shield against ionising radiation
6 Vacuum pump
7 Self-sealing connecting piece
8 Isolator
9 Device for membrane filtration

The invention claimed is:

1. A method for testing the sterility of a radioactive substances, comprising the steps of:
    a) performing membrane filtration of a solution of a radioactive substance by means of a device for membrane filtration comprising at least one membrane filter in an isolator (8), and extraction by suction through a system comprising:
        a filtrate bottle (1) comprising at least one liquid-conveying line (2) and at least one pressure equalizing line (3),
        at least one transport carriage (4), wherein the filtrate bottle is on the at least one transport carriage (4), wherein the transport carriage (4) is movable, wherein at least the filtrate bottle (1) is surrounded by a shield against ionising radiation (5),
        a vacuum pump (6), wherein the vacuum pump (6) is connected to the at least one liquid-conveying line (2) and is suitable for pumping filtrate containing the radioactive substance into the filtrate bottle (1),
        at least one self-sealing connecting piece (7), and
        an isolator (8), wherein the isolator (8) is connected to the filtrate bottle (1) on the at least one transport carriage (4) via the at least one liquid-conveying line (2) and the at least one pressure equalizing line (3), wherein the isolator (8) comprises a device for membrane filtration (9), wherein the at least one self-sealing connecting piece (7) connects the filtrate bottle to the isolator (8) via the at least one liquid-conveying line (2) and/or the at least one pressure-equalising line (3),
    b) culturing the at least one membrane filter& in a culture medium, and
    c) testing the culture medium for microorganisms.

2. The method according to claim 1, wherein the solution of a radioactive substance is an aqueous solution, alcoholic solution and/or oil-based solution.

3. The method according to claim 1, wherein culturing the at least one membrane filter in step b) is carried out at a temperature in the range of 20° C. to 37° C., at an air humidity in the range of 30% to 70%, and/or for a duration of 14 days.

4. The method according to claim 1, further comprising sucking the solution of a radioactive substance from the filtrate bottle and allowing the solution of a radioactive substance to decay in a decay tank.

5. The method according to claim 1, wherein the radioactive substances is selected from radioactive pharmaceuticals and/or diagnostic agents.

6. The method according to claim 3, further comprising sucking the solution of a radioactive substance from the filtrate bottle and allowing the solution of a radioactive substance to decay in a decay tank.

7. The method according to claim 3, wherein the radioactive substances is selected from radioactive pharmaceuticals and/or diagnostic agents.

8. A system for testing the sterility of radioactive substance&, comprising:
    i. a filtrate bottle (1) comprising at least one liquid-conveying line (2) and at least one pressure equalizing line (3),
    ii. at least one transport carriage (4), wherein the filtrate bottle is on the at least one transport carriage (4), wherein the at least one transport carriage (4) is movable, wherein at least the filtrate bottle (1) is surrounded by a shield against ionising radiation (5), iii. a vacuum pump (6), wherein the vacuum pump (6) is connected to the at least one liquid-conveying line (2) and is suitable for pumping into the filtrate bottle (1) filtrate containing the radioactive substance, iv. at least one self-sealing connecting piece (7), and v. an isolator (8), wherein the isolator (8) is connected to the filtrate bottle (1) on the at least one transport carriage (4) via the at least one liquid-conveying line (2) and the at least one pressure equalizing line (3), wherein the isolator (8) comprises a device for membrane filtration (9), wherein the at least one self-sealing connecting piece (7) connects the filtrate bottle to the isolator (8) via the liquid-conveying line (2) and/or the pressure-equalising line (3).

9. The system according to claim 8, wherein the shield against ionising radiation (5) comprises a metal layer and a plexiglass layer.

10. The system according to claim 8, wherein the shield against ionising radiation (5) comprises a metal having a thickness in the range of 40 mm to 100 mm.

11. The system according to claim 8, wherein the filtrate bottle (1) is made of glass, plastic and/or metal.

12. The system according to claim 8, wherein the filtrate bottle (1) comprises a liquid fill level meter, wherein the liquid fill level meter emits an optical and/or acoustic signal at a predefined fill level of the filtrate.

13. The system according to claim 8, wherein the at least one liquid-conveying line and the at least one pressure equalizing line are made of rubber and/or metal.

14. The system according to claim 8, wherein the connection between the isolator (8) and the filtrate bottle (1) on the transport carriage is designed as a beam trap.

15. The system according to claim 8, wherein the device for membrane filtration (9) comprises at least one membrane filter made of cellulose acetate or cellulose nitrate and/or having pores in the range of 0.2 to 0.45 µm.

16. The system according to claim 10, wherein the filtrate bottle (1) is made of glass, plastic and/or metal.

17. The system according to claim 10, wherein the filtrate bottle (1) comprises a liquid fill level meter, wherein the liquid fill level meter emits an optical and/or acoustic signal at a predefined fill level of the filtrate.

18. The system according to claim 10, wherein the liquid-conveying line and the at least one pressure equalizing line are made of rubber and/or metal.

19. The system according to claim 10, wherein the connection between the isolator (8) and the filtrate bottle (1) on the transport carriage is designed as a beam trap.

20. The system according to claim 10, wherein the device for membrane filtration (9) comprises at least one membrane filter made of cellulose acetate or cellulose nitrate and/or having pores in the range of 0.2 to 0.45 µm.

\* \* \* \* \*